United States Patent [19]

Van Noord

[11] Patent Number: 5,246,440
[45] Date of Patent: Sep. 21, 1993

[54] ELECTROSURGICAL KNIFE

[76] Inventor: Andrew J. Van Noord, 1434 Hillsboro Ave., SE., Grand Rapids, Mich. 49506

[21] Appl. No.: 582,376

[22] Filed: Sep. 13, 1990

[51] Int. Cl.$^5$ ............................................. A61B 17/36
[52] U.S. Cl. ..................................... 606/39; 606/42; 606/45
[58] Field of Search ...................... 606/34, 37, 39, 41, 606/45, 46, 49, 167, 170; 604/20-22, 35, 902

[56] References Cited

U.S. PATENT DOCUMENTS

| | | |
|---|---|---|
| 2,012,363 | 8/1935 | Vogel. |
| 2,196,171 | 4/1940 | Arnesen. |
| 2,275,167 | 3/1942 | Bierman. |
| 2,828,747 | 4/1958 | August. |
| 2,888,928 | 6/1959 | Seiger. |
| 3,035,580 | 12/1960 | Guiorguiev. |
| 3,595,239 | 7/1971 | Petersen. |
| 3,614,414 | 10/1971 | Gores. |
| 3,614,415 | 10/1971 | Edelman. |
| 3,626,471 | 12/1971 | Florin. |
| 3,648,001 | 3/1972 | Anderson et al.. |
| 3,758,951 | 9/1973 | Scrivo et al.. |
| 3,801,766 | 4/1974 | Morrison, Jr.. |
| 3,825,004 | 7/1974 | Durden, III. |
| 3,828,780 | 8/1974 | Morrison, Jr.. |
| 3,847,153 | 11/1974 | Weissman. |
| 3,858,577 | 1/1975 | Bass et al.. |
| 3,858,586 | 1/1975 | Lessen. |
| 3,906,955 | 9/1975 | Roberts ................................. 604/21 |
| 3,920,022 | 11/1975 | Pastor. |
| 3,945,375 | 3/1976 | Banko. |
| 3,974,833 | 8/1976 | Durden, III. |
| 4,040,426 | 8/1977 | Morrison, Jr.. |
| 4,074,718 | 2/1978 | Morrison, Jr.. |
| 4,307,720 | 12/1981 | Weber, Jr. ............................ 604/22 |
| 4,445,517 | 5/1984 | Feild ................................... 128/752 |
| 4,449,528 | 5/1964 | Auth et al.. |
| 4,517,974 | 5/1985 | Tanner. |
| 4,562,838 | 1/1986 | Walker ................................. 606/45 |
| 4,642,090 | 2/1987 | Utrata ................................. 604/22 |
| 4,919,129 | 4/1990 | Weber, Jr. et al. .................. 606/42 |

FOREIGN PATENT DOCUMENTS 1007960 5/1957 Fed. Rep. of Germany.
57862 9/1953 France.

OTHER PUBLICATIONS

Walker Medical Instruments brochure, "Lapin Clear Cut II".
Walker Medical Instruments brochure, "Hand Held Fluid Suction With Fiberoptic Light".

Primary Examiner—Peter A. Aschenbrenner
Attorney, Agent, or Firm—Varnum, Riddering, Schmidt & Howlett

[57] ABSTRACT

An electrosurgical knife having an elongated knife handle of simple construction and inexpensive to manufacture has an opening at one end for accommodating an electrosurgical electrode and electric switches for controlling the application of current to the electrode. The handle is provided with a pair of grooves, one for optionally retaining an optical conduit and the other for optionally retaining a fluid-transporting tube. Both the optical conduit and the tube can slide in the grooves, allowing them to be readily adjusted to be adjacent the distal end of electrodes of varying lengths.

The knife handle has an internal passageway extending the length of the handle for accommodating electrical conductors and a printed circuit board. The handle further has an enlarged section for enclosing a pair of push-button switches with exposed outer surfaces. Electrical connections may be established between the electrical conductors and the electrosurgical blade on the circuit board by operating the switches. The knife handle has two substantially symmetrical elongated sections joined along the length of the handle. Each of the sections has areas defining a portion of the two grooves and of the passageway. The knife handle may be readily assembled by inserting the electrical devices, such as the conductors, the circuit board and the switches in one half of the knife and joining the other half of the knife to it.

15 Claims, 3 Drawing Sheets

ELECTROSURGICAL KNIFE

BACKGROUND OF THE INVENTION

1. Field of the Invention

This invention relates to surgical instruments and more particularly to an improved electrosurgical knife.

2. Prior Art

Electrosurgery is a well-known technique in which a high-frequency electrical current is conducted through a surgical instrument into the tissue of a patient to effect electrocoagulation and/or electrocauterization. In electrosurgery, the surgical instrument and the patient are both connected to a source of high-frequency current, and the instrument is provided with a metallic device such as a blade, that functions as an electrode for conducting the high-frequency current to the tissue of the patient. As the surgeon brings the electrode in contact with the tissue, the current passes through the patient to a second electrode connected elsewhere to the body of the patient to complete the current path back to the source of high-frequency current. Because the point of contact between the instrument electrode and the patient is comparatively small, the relative current density and electrical resistance are comparatively high, resulting in electrocoagulation and/or electrocauterization at the point of contact.

One of the advantages of electrosurgery is that it allows the surgeon to perform very exact surgery by touching the electrode blade to the precise area to be treated. A disadvantage of this type of surgery, however, is that the flow of current through the tissue often generates smoke in the vicinity of the electrode. Except in well ventilated areas, the smoke tends to block the view of the surgeon. A more serious concern is that the smoke may be contaminated with viruses from the patient which may be transmitted to anyone who inadvertently inhales the smoke. To protect the medical staff from exposure to the virus of deadly or crippling diseases, it is important to aspirate the smoke from the immediate surgical area before it dissipates into the air breathed by the attendants. To solve this problem, it is sometimes necessary to have a separate attendant hold an aspiration tube adjacent the electrode while the surgeon is performing the operation. The disadvantages of such an arrangement are obvious. The electrosurgical technique may be used for sealing off blood vessels and hence, the surgeon may be required to operate in an area where blood tends to accumulate and particulates may be collected. Accordingly, it is desirable to have a means for removing accumulated blood and particulates as well as smoke from the surgical area. In an analogous fashion, some surgical procedures may require an additional source of light so that the surgeon may be able to adequately view the area to be treated, while in other situations no such additional light is required.

Examples of patents disclosing prior art electrosurgical instruments are as follows:

U.S. Pat. No. 3,828,780 to C. F. Morrison, Jr. (dated Aug. 13, 1974) describes a combined electrosurgical and suction instrument. The instrument consists essentially of an elongated body having a hollow metal tube with a distal end functioning as the electrode and having a proximal end connected to an electrical wire in the housing. Suction is applied to the proximal end of the hollow metal tube so as to remove fluids through the tube electrode.

U.S. Pat. No. 3,825,004 to J. G. Durden III (dated Jul. 23, 1974) discloses a disposable electrosurgical cautery having a handle constructed of upper and lower halves forming a cavity for accommodating a hollow metal tube. The distal end of the tube is used as the electrode and the proximal end is connected to an electrical wire and a vacuum hose to withdraw fluids through the tube electrode.

U.S. Pat. No. 3,906,955 to R. R. Roberts (dated Sep. 23, 1975) discloses an electrosurgical tool having a housing with an electrode disposed at the distal end of the housing and connected to electrical wiring within the housing. A separate vacuum tube contained within the housing and extending beyond the distal end of the housing is disposed adjacent the electrode to withdraw fluid from the cutting area. The housing is provided with a manually-operable slide which is rigidly attached to the vacuum tube internal to the housing and which may be used to position the distal end of the vacuum tube within the range of travel of the manually-operable slide.

U.S. Pat. No. 3,974,833 to J. G. Durden III (dated Aug. 17, 1976) discloses a surgical knife with a combination cutting electrode and vacuum tube such as that disclosed in U.S. Pat. No. 3,825,004 referenced above, and is further provided with an aperture in the knife handle communicating with an opening in the vacuum tube. By selectively covering the aperture in the handle with a finger, the surgeon controls the amount of suction applied to the surgically treated area.

U.S. Pat. No. 4,562,838 to W. S. Walker (dated Jan. 7, 1986) discloses an electrosurgical knife having a generally cylindrical housing and an electrode extending from a central opening in the housing at the distal end thereof. The housing is provided with a number of ducts at the distal end thereof in communication with a cavity internal to the housing. A hose, which may be either connected to a sterile air-pressure source or a vacuum source, is connected to the fluid cavity within the housing and may be used to aspirate smoke or to distribute an airflow in the area of the surgical blade. The housing is further provided with a mounting channel along its upper edge for slidably receiving a light-transmitting cable of a fiber-optic system to illuminate the region around the cutting blade.

Disadvantages of these and other prior art devices are that the electrosurgical knives have become relatively bulky and complex structures which are not inexpensive to manufacture. The prior art devices are often difficult to hold and lack the flexibility that is desired by many surgeons. Surgeons in a number of hospitals use the less expensive standard electrosurgical knives which do not have the aspirating capability or a separate light source to perform operations in well-ventilated and well-lighted areas, and use the more expensive, specialized knives only when required. This means that the hospitals must have multiple inventories. It is therefore desirable to provide a surgical knife which is inexpensive and optionally provides the capabilities of the more specialized knives.

A particular disadvantage of prior art electrosurgical knives is the inability to withdraw smoke and other fluid and particulates from the immediate vicinity of the electrode when electrodes of different types and lengths are used. The distance of the electrode from the knife handle may vary greatly, e.g., from approximately 1 inch to over 12 inches. The shape of the electrodes may be that of a tube, a flat blade, a loop, a needle, or other configurations. Prior art devices do not provide an electrosurgical knife which is readily adaptable to provide aspiration at the surgical contact area for the various electrodes used in electrosurgery.

SUMMARY OF THE INVENTION

These and other problems of the prior art are overcome in accordance with my invention by means of an electrosurgical knife having an elongated knife handle of simple construction and having one surface, extending generally parallel to a longitudinal centerline of the knife handle, comprising a retainer for optionally retaining a fluid-transporting tube of a selected length for removing smoke and blood and particulates from the distal end of the electrode. A second surface extending generally parallel to the longitudinal centerline comprises a retainer for optionally retaining an optical conduit for providing illumination at the distal end of the electrode. The knife handle is ergonomically shaped by the formation of lower outer side walls which present substantially flat surfaces for engagement by the digits of the surgeon's hand. Advantageously, in accordance with this invention, the knife handle is simple in structure and inexpensive to manufacture and is shaped to give the surgeon better control and a less tiresome hold of the knife. The knife may be used by surgeons as a standard inexpensive electrosurgical knife or with an optional fluid-transporting tube when the surgeon considers that aspiration or flushing of the area of surgery is required. Similarly, when a surgeon has to operate in areas of insufficient light, an optical conduit connected to a light source may be readily inserted in the handle to provide the necessary light at the point of operation.

In accordance with one aspect of the invention, the fluid-transporting tube and the optical conduit engage channels on the outside of the handle in a slidable fashion. Advantageously, this allows the surgeon to position the optical conduit to best illuminate the work area. It further allows the fluid-transporting tube to be adjusted at a position adjacent to or beyond the end point of the electrode to inject a flushing solution or to remove liquids and particulate which may collect in an area below the electrode. Advantageously, the electrosurgical knife of this invention can accommodate surgical electrodes of differing lengths and the adjustability of the fluid-transporting tube and the optical conduit provides the ability to precisely position those devices relative to electrodes of different lengths. Furthermore, fluid-transporting tubes of different lengths may be selectively inserted in the knife handle and extended beyond the end of the electrode for use in deep surgery to evacuate lower areas. Advantageously, the extension distance is limited only by the length of the tube used and is not restricted by any feature of the handle or configuration of the cutting electrode.

In accordance with one aspect of the invention, the knife handle comprises a longitudinally extending internal passageway extending between the proximal end and the distal end of the handle and an electrical connecting device disposed in the passageway for establishing an electrical connection between a conductor at the distal end of the knife handle and the blade electrode. Advantageously, the handle comprises two substantially symmetrical elongated sections joined at a seam extending in a generally vertical plane which includes the longitudinal centerline of the handle. Each of the symmetrical sections comprises areas defining a portion of the two grooves and the passageway.

In accordance with one aspect of the invention, the handle comprises an inner spatial area, a first passageway section extending from the proximal end to the inner spatial area and a second passageway section extending from the distal end to the inner spatial area, and the first and second passageway sections and the inner spatial area are in substantially linear alignment, further simplifying the structure of the knife handle.

In accordance with one aspect of the invention, an electrical connecting device is disposed in the passageway for establishing an electrical connection between a conductor connected to the distal end of the knife handle and a socket for receiving an electrosurgical electrode in the distal end. The interconnecting device comprises a circuit board, disposed in the inner spatial area and connected to the conductor and the socket, and at least one actuating member. Electrical connections may be selectively made on the circuit board between the conductor at the distal end and the socket by operation of the actuating member to provide electrical power to an electrode inserted in the socket. Advantageously, the inner spatial area is provided with flanges for retaining the circuit board and the actuating member. The knife handle is further provided with an enlarged section for accommodating the inner spatial area disposed below an upper surface area which extends over a portion of the one groove. The enlarged section is provided with an opening in alignment with the one groove optionally for accommodating an optical conduit in that groove. The upper surface area of the knife handle is provided with openings, and the actuating members include push buttons extending through the openings in the upper surface area. Each actuating member comprises a rigid structure extending downwardly below the flat surface area and intersecting the one groove. The rigid structure of each of the actuating members is provided with an opening in alignment with the one groove to allow the passage of an optical conduit. Furthermore, the opening in each of the rigid structures is elongated in the vertical direction to allow movement of the actuating device in the presence of an optical conduit in the one groove. Each actuating member extends from the flat upper surface area to the circuit board and establishes an electrical connection on the circuit board between predetermined electrical contact points when the actuating member is operated. Spring action returns the actuated member to a position away from the circuit board, in which the electrical circuit is in a disconnected state.

Advantageously, the substantially symmetrical sections of the knife handle include flanged areas for engaging the printed circuit board and actuating members. The knife handle may be readily assembled by inserting the circuit board, connected to the blade socket at the distal end and the conductor at the proximal end, in the longitudinal passageway and engaging the circuit board and actuating members with flanges of one of the handle halves and adding the other half. In this manner, an inexpensive electrosurgical knife is provided which includes a switching mechanism for selectively applying electrical current from a plurality of current sources to a blade electrode and which may be optionally provided with an illuminating device and a flushing/aspirating device.

BRIEF DESCRIPTION OF THE DRAWING

An illustrative embodiment of the invention is described below with reference to the drawing in which.

DETAILED DESCRIPTION

Figure 1:
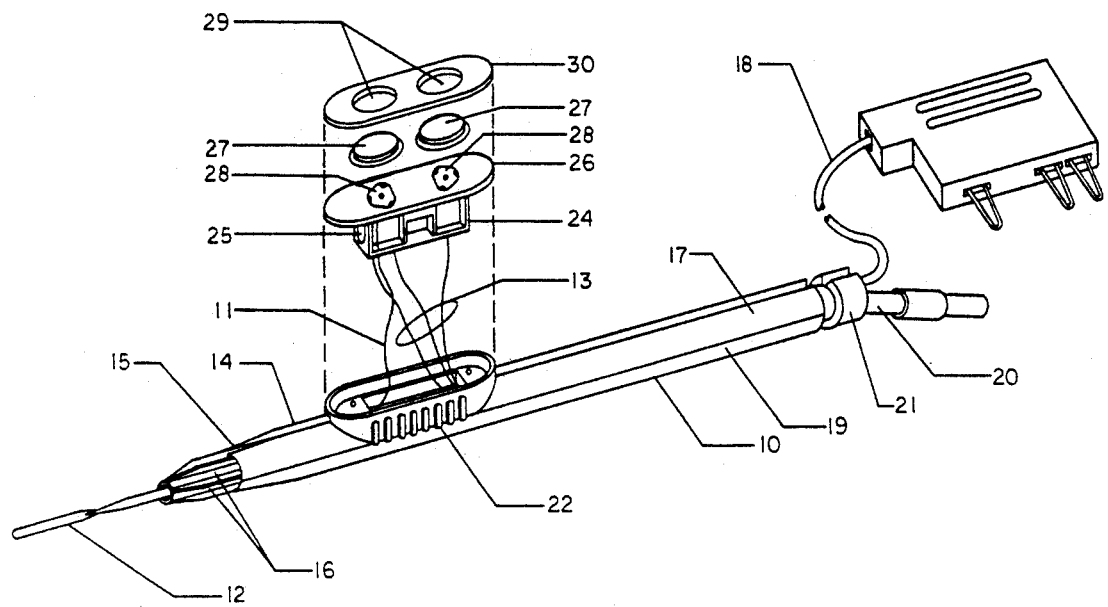
FIG. 1 is a perspective view of a prior art electrosurgical knife.

FIG. 1 is a representation of a prior art electrosurgical knife comprising a housing 10. An electrosurgical electrode 12 in the form of a flat blade is inserted in the distal end of the housing 10 and is electrically connected by a wire 11 to a printed circuit board 26. An electrical conductor 18 is attached to the proximal end of the housing 10 and is connected by wires 13 to a printed circuit board 26. A pair of switch contacts 28 are selectively activated by operation of push buttons 27 to interconnect predetermined ones of the wires 13 to the wire 11 to provide a connection to a number of different current sources via conductor 18. The printed circuit board 26 is supported by a housing 24 which is contained within an enlarged area 22 of the housing 10 when the device is assembled. The housing 10 is provided with an upper groove 14 for accommodating an optical conduit for the purpose of illuminating the area in the vicinity of the electrode 12. The groove 14 extends through the enlarged area 22 and the structure 24 is provided with a passageway 25 for accommodating an optical conduit. A cap 30 is designed to fit within the top portion of the expanded area 22 to cover the printed circuit board 26 while allowing access to the buttons 27, which extend through openings 29 when the arrangement is fully assembled. The housing 10 consists of an upper half 17 and a lower half 19 which are welded together to form the housing 10. The housing 10 is essentially hollow, and an end piece 21 is formed integral with a tube connection section 20, which may be connected to a vacuum source. A nose piece 15 is inserted in the distal end of the housing 10 and is provided with a plurality of grooves 16 which communicate with the hollow interior structure of the housing 10. When vacuum is applied t o the tubular section 20, which also communicates with the interior of the housing 10, smoke is withdrawn from the distal end of the handle via the openings provided by grooves 16 and is conducted through the interior of the housing 10 and withdrawn via tubular section 20. It will be apparent that the prior art device, which is assembled of molded parts, will require several such parts. The top half and bottom half of the housing 10, the nose piece 15, and the end piece 21 all have to be separately molded and separately attached at time of assembly. The support structure 24 needs to be separately molded as well, and is fastened to the bottom of the circuit board 26 while the cap 30 is glued to the top of the circuit board 26. It will be apparent that manufacture of the prior device requires the separate manufacture of a number of independent components which have to be assembled by means of several separate assembly steps.

Figure 2:
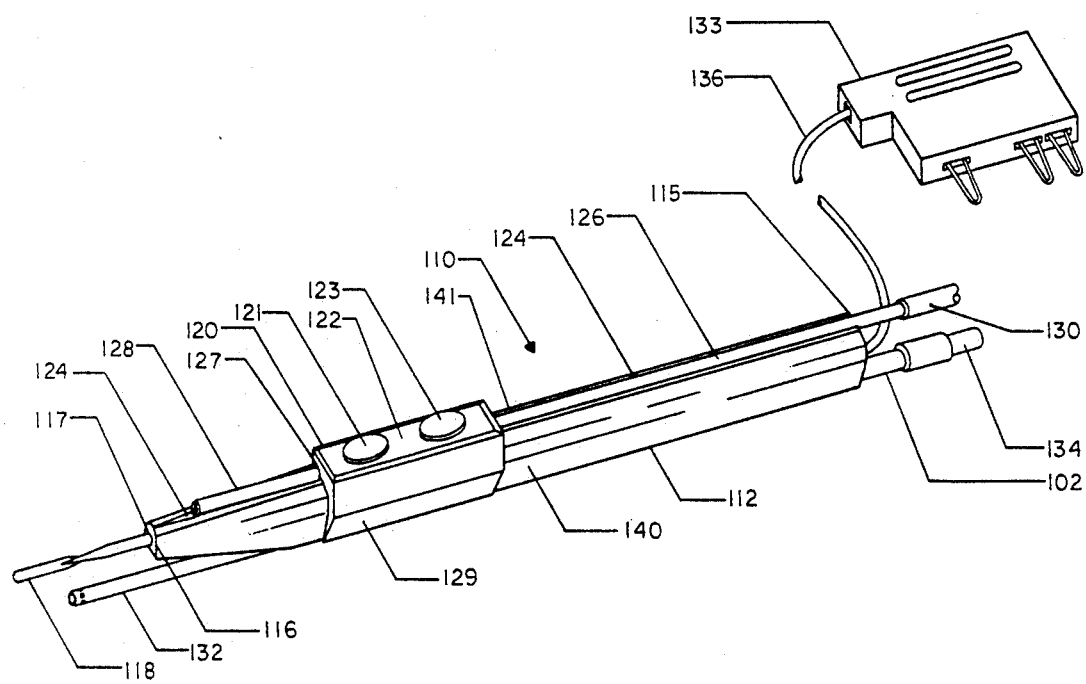
FIG. 2 is a perspective drawing of an electrosurgical knife embodying the principles of this invention.

FIG. 2 is a perspective view of an illustrative embodiment of an electrosurgical knife in accordance with my invention. The electrosurgical knife, generally indicated at 110 includes an elongated handle 112, comprising left and right substantially symmetrical handle sections 140, 141. The handle 112 comprises a distal end 116 provided with an opening 117 for receiving an electrosurgical electrode 118 and a proximal end 115 provided with an electrical conductor 136. In this illustrative embodiment, the electrode 118 is in the form of a blade. The handle 112 is provided with an upwardly extending enlarged section 120 having an upper surface area 122. A pair of push buttons 121, 123, shown in greater detail in FIG. 7, for controlling the application of electrical energy from conductor 136 to electrode 118, extend through corresponding openings in the surface area 122. When in use, the enlarged section 120 of the electrosurgical knife will usually be held between the surgeon's thumb and fingers. The surgeon's thumb and middle finger will rest on especially provided slanted surfaces 129 on the lower left- and right-hand sides of the enlarged section 120. The index finger will be used to operate push-button switches 121 and 123. A longitudinally extending groove 124 extends along the top surface of handle 112 for retaining therein a fiberoptic optical conduit 126 having a distal end 128 disposed in the vicinity of the cutting electrode 118. The optical conduit 126 is connected via an optical cable 130 to an optical source. The optical conduit 126 is slidably retained in groove 124 and extends through an opening 127 in the enlarged section 120 and below the surface area 122, such that the optical conduit 126 may be slidably disposed in groove 124 to any desirable position relative to the distal end of electrode 118. FIG. 2 further shows a fluid-transporting tube 132 slidably supported by handle 112. Tube 132 is adjustably supported in handle 112 to allow its distal end to be moved to any desired position with respect to and in proximity of the distal end of the electrode 118. Fluid-transporting tube 132 may be connected to a fluid-transporting hose 134, connected to a vacuum source, to safely remove any virus contaminated smoke or liquids and particulate from the surgical area proximate to the distal end of the electrode. The fluid-transporting tube 132 may also be used for injecting a cleansing solution such as a rinsing or flushing solution into the surgical area by connecting the fluid-transporting hose 134 to a source of cleansing solution.

Figure 3:
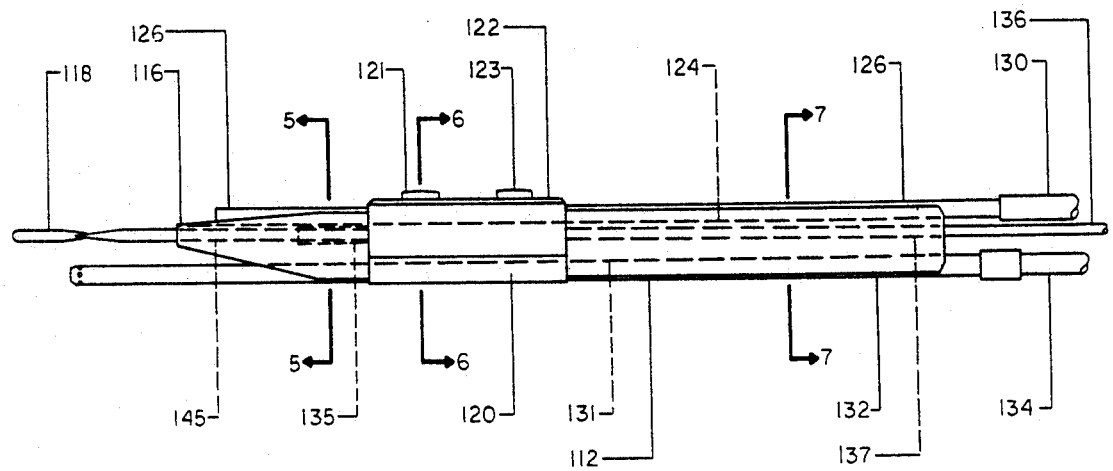
FIG. 3 is a left side elevation of the electrosurgical knife of FIG. 2.
Figure 4:
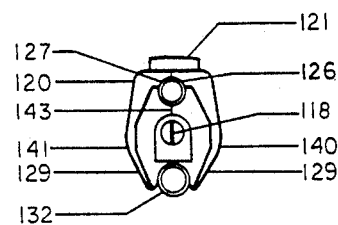
FIG. 4 is a frontal elevation of the electrosurgical knife of FIG. 2, viewed from the distal end.

FIG. 3 is a left side elevation of the electrosurgical knife shown in FIG. 2 showing, in dashed lines, upper groove 124, slidably retaining the optical fiber conduit 126 and a lower groove 131 slidably retaining the fluid-transporting tube 132. Optical conduit 126 may be any of a number of commercially available fiber-optic conductors encased in a generally rounded conduit. Tube 132 may be made of any suitable material preferably of low electrical conductivity, such as a hard plastic, to reduce the possibility of arcing when the tube is extended to a position adjacent electrode 118. As is apparent from the drawing, grooves 124 and 131 extend the full length of the handle 112. In the area of the enlarged section 120, the groove 124 extends through the enlarged area and below flat upper surface area 122 through which buttons 121 and 123 extend. An electrical socket 135 receives one end of electrode 118. Socket 135, which is selectively connected to one or more electrical wires in conductor 136 by operation of buttons 121, 123, provides electrical connection to electrode 118. FIG. 4 is a front elevation of the surgical knife of FIG. 2 more clearly showing the enlarged section 120 containing buttons 121 and 123 and showing the optical conduit 126 extending through opening 127 of the enlarged section 120.

Figure 5:
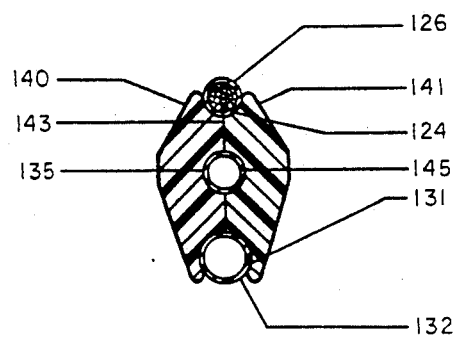
FIG. 5 is a cross-sectional view along line 5—5 of FIG. 3.

The surgical knife in accordance with this invention has a simplified construction and consists essentially of two molded sections joined along a vertically extending plane along the longitudinal centerline of the handle. The configuration is illustrated in FIGS. 5 though 8. FIG. 5 is an enlarged cross sectional view taken along line 5—5 of FIG. 3. As is apparent from the drawing, the handle 112 comprises two substantially symmetrical handle sections 140 and 141 joined along centerline 143. When assembled, the two halves 140 and 141 define grooves 124 and 131 for accommodating optical conductor 126 and fluid-transporting tube 132, respectively. A central opening 145 provides a passageway section extending from enlarged section 120 to the distal end 116, to accommodate electrode 118 and electrical socket 135 in which electrode 118 is inserted.

Figure 6:
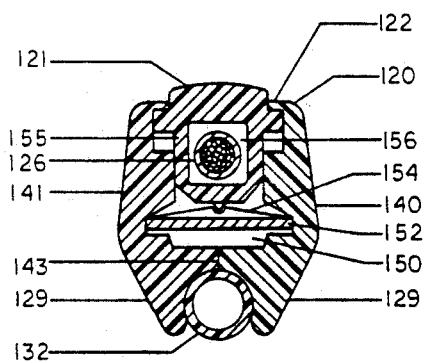
FIG. 6 is a cross-sectional view along line 6—6 of FIG. 3.
Figure 7:
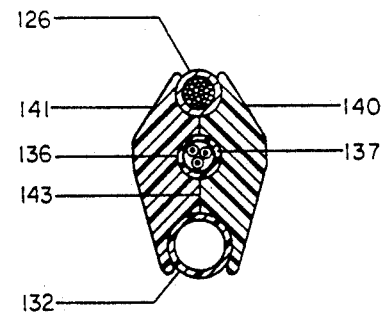
FIG. 7 is a cross-sectional view along line 7—7 of FIG. 3.

FIG. 6 presents an enlarged cross sectional view taken along line 6—6 of FIG. 3, extending through push button 121. FIG. 6 shows that the enlarged section 120 has an inner spatial area 150 under upper surface 122. Spatial area 150 is configured to accommodate a horizontally extending printed circuit board 152 and downwardly extending rigid structure 155 of switch button 121. The switch button 121, serves to interconnect contact points on the circuit board 152 when depressed. It serves to actuate a well-known metallic contact disk 154 biased toward a position away from the circuit board. When switch button 121 is released, it is returned to the disconnect state by the spring action of contact disk 154 and the electrical connection is broken. The rigid structure 155 of switch button 121 is provided with a central opening 156 to accommodate passage of optical conduit 126. Opening 156 is elongated in the vertical direction to allow movement of the button 121 in the vertical direction when conduit 126 is positioned in groove 124. Switch button 123 is constructed and operates in the same manner. It will be apparent from FIG. 6, that handle 112 consists of substantially symmetrical body halves 140 and 141, joined along seam 143. FIG. 7, which is an enlarged cross sectional view of the handle 112 along line 7—7 of FIG. 3, further shows the basic construction of the handle 112, consisting of body halves 140 and 141 joined along seam 143. Shown in FIG. 7 is a passageway section 137 extending from inner spatial area 150 to the proximal end 115 of handle 112 to accommodate electrical wires of conductor 136.

Figure 8:
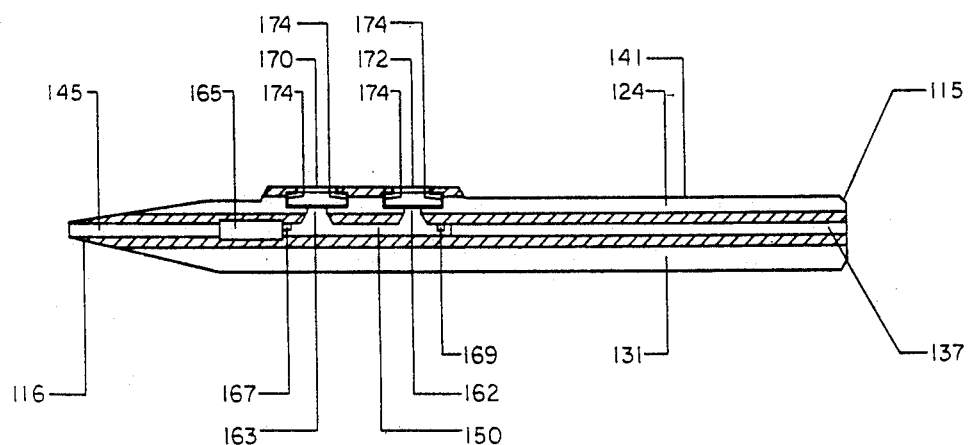
FIG. 8 is a longitudinal cross-sectional view of one of the two halves of the knife handle.
Figure 9:
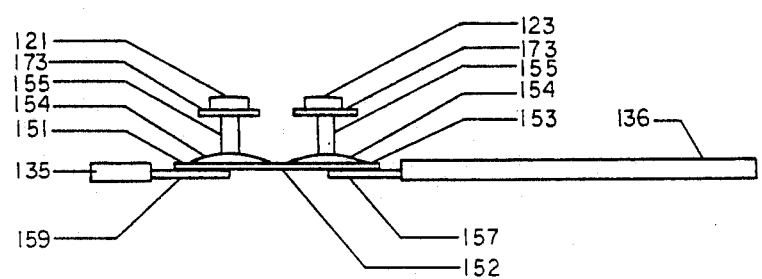
FIG. 9 is a representation of a connecting device for an electrosurgical knife handle in accordance with the invention.

FIG. 8 is a side elevation of the right-hand handle section 141, which is one of two substantially symmetrical half sections from which handle 112 is constructed. FIG. 9 shows an electrical connecting device consisting of the circuit board 152, switch buttons 121 and 123, conductor 136 and electrical socket 135. The two symmetrical section 140, 141 are adapted to receive the structure of FIG. 9. The knife handle in accordance with this invention may be assembled by inserting the electrical connecting device of FIG. 9 in one of the symmetrical sections, e.g., the right-hand section 141 shown in FIG. 8, and joining the left-hand mirror image section 140, to complete the assembly of the knife handle. The two half sections will be joined along a vertically extending plane which includes the longitudinal centerline of the knife handle. In FIG. 8, vertically extending surfaces along which right-hand section 141 is joined to a left-hand section are shown in crosshatch.

The circuit board 152 will be positioned in inner spatial area 150 of right-hand section 141, which is provided with downwardly extending flanges 167, 169 for engaging upper end surfaces 151, 153 respectively of circuit board 152. Spatial areas 162, 163 are provided in section 141 to accommodate the downwardly extending structures 155 of switch buttons 121, 123 respectively. Handle section 141 is provided with flanged areas 174 for engaging corresponding flanges 173 on buttons 121 and 123. Openings 170 and 172 accommodate the upper portions of buttons 121 and 123 respectively such that the top portions of these buttons are exposed for pushbutton operation. Inner spatial area 150 of handle section 141 communicates with a passageway section 137 extending from the inner spatial area 150 to the proximal end 115. In similar fashion, inner spatial area 150 communicates with another passageway section 145 extending to the distal end 116. The passageway section 145 is provided with an enlarged section 165 to accommodate electrical socket 135 into which the electrode 118 is inserted. The inner spatial area and the passageway sections extending to the distal and proximal ends are in substantially linear alignment, further simplifying the structure of the knife handle.

The conductor 136 may contain a plurality of wires connected to different current sources providing current of different characteristics. For example, one source may provide current used for cutting and another for cauterizing, etc. The separate wires of conductor 136 will be electrically connected to the circuit board 152, as shown at 157. Electrical connections are made through circuit board 152 in a standard fashion to conductors on its top surface which may be selectively connected to electrical socket 135 by appropriate operation of buttons 121 and 123. Socket 135 is shown connected to the circuit board 152 at 159. Accordingly, electrical currents of differing characteristics, may be selectively applied to the electrode, thereby selectively providing differing types of energy for different surgical applications.

It will be understood that the embodiments disclosed herein are only illustrative of the principles of the invention and that numerous other configurations may be devised by those skilled in the art without departing from the spirit and scope of the invention.

What is claimed is:

1. An electrosurgical knife handle comprising:
    a longitudinally extending housing having a distal end and a socket for receiving an electrosurgical electrode in said distal end and a proximal end and an electrical conductor at said proximal end;
    a passageway extending longitudinally within said housing between said proximal end and said distal end and an electrical connecting device disposed in said passageway for establishing an electrical connection between said conductor and said socket;
    a first surface external to said housing extending generally parallel to a longitudinal centerline extending from said proximal end to said distal end, and comprising first retaining means formed on said first surface for optionally retaining an optical conduit;

a second surface external to said housing opposite said first surface and extending generally parallel to said longitudinal centerline and comprising second retaining means formed on said second surface for optionally retaining a fluid-transporting tube;

said housing comprising two substantially symmetrical elongated sections joined at a seam extending in a generally vertical plane which includes said longitudinal centerline of said housing, each of said sections comprising areas defining a portion of each of said first and second retaining means and of said passageway.

2. The electrosurgical knife handle in accordance with claim 1 wherein said first retainer for optionally retaining an optical conduit comprises a first groove formed in said first surface and wherein said second retainer for optionally retaining said fluid-transporting tube comprises a second groove formed in said second surface.

3. The electrosurgical knife handle in accordance with claim 2 comprising a surface area partially enclosing said first groove and an opening in said surface area, and wherein said electrical connecting device comprises an actuating member disposed below said surface area and operable to selectively establish electrical connections in said electrical connecting device, said actuating member accessible through said opening and comprising a rigid structure extending downwardly below said surface area and intersecting said first groove, said structure having an opening therein in alignment with said first groove to allow passage of said optical conduit through said structure.

4. The electrosurgical knife handle in accordance with claim 3 wherein said opening in said structure is elongated in the vertical direction to allow movement of said actuating member in the vertical direction in the presence of said optical conduit.

5. The electrosurgical knife handle in accordance with claim 3 wherein said passageway includes an inner spatial area below said surface area and said first groove and wherein said connecting device further comprises a printed circuit board disposed in said spatial area below said first groove, said printed circuit board connected to said conductor and said socket, and wherein said actuating member extends to said circuit board to establish an electrical connection on said circuit board between said conductor and said socket when said actuating member is operated.

6. The electrosurgical knife handle in accordance with claim 5 wherein said connecting device further comprises a contact device biased in a direction away from said printed circuit board and tending to return said actuating member to a disconnected position.

7. The electrosurgical knife handle in accordance with claim 5 wherein said conductor comprises a plurality of individual wires connected to said printed circuit board and said actuating member is operable to selectively connect individual ones of said wires to said socket on said circuit board.

8. The electrosurgical knife handle in accordance with claim 7 wherein said actuating member comprises two push buttons, each having a rigid structure with an opening elongated in the vertical direction to allow for passage of said optical conduit.

9. The electrosurgical knife handle in accordance with claim 7 comprising a surface area partially enclosing said first groove, and wherein said passageway comprises an inner spatial area disposed below said surface area and said connecting device comprises a circuit board and a switch for selectively establishing electrical connections on said circuit board disposed within said spatial area, and said passageway further comprising a first passageway section extending from said proximal end to said inner spatial area and a second passageway section extending from said distal end to said inner spatial area, said first and said second passageway sections being in substantially linear alignment.

10. The electrosurgical knife handle in accordance with claim 9 wherein said connecting device further comprises an electrical connection from said conductor to said circuit board and an electrical connection from said circuit board to said socket and wherein said inner spatial area comprises flanges for engaging said circuit board and said switch, whereby said handle is assembled by inserting said connecting device and said socket in one of said substantially symmetrical sections and joining the other of said sections thereto.

11. The electrosurgical knife handle in accordance with claim 2 wherein said first groove for retaining said optical conduit and said second groove for retaining said fluid-transporting tube are designed to slidably retain said optical conduit and said fluid-transporting tube, respectively.

12. The electrosurgical knife handle in accordance with claim 1 wherein said fluid-transporting tube has a substantially circular cross section, and said second retainer for retaining said tube comprises a groove in said second surface having side walls partially conforming to said cross section, thereby partially encircling said tube when said tube is inserted in said groove.

13. The electrosurgical knife handle in accordance with claim 12 wherein said distal end of said housing comprises a lower tapered section having an angle taper from an outer edge of said groove for retaining said tube to an inner edge of said groove for retaining said tube.

14. The electrosurgical knife handle in accordance with claim 1 wherein said electrical connecting device comprises an actuating member operable to selectively establish electrical connections in said electrical connecting device and said housing comprises a housing section having a top surface for providing external access to said actuating member, said housing section having outer walls having substantially flat portions slanting at a predetermined angle with respect to a vertical centerline through said housing for providing support surfaces for the digits of a surgeon's hand.

15. An electrosurgical knife comprising:
a longitudinally extending housing having a distal end and an electrosurgical electrode extending from said distal end, and a proximal end having an electrical conductor connected thereto;
a passageway extending longitudinally within said housing between said proximal end and said distal end and an electrical connecting device disposed in said passageway for establishing an electrical connection between said conductor and said electrode;
a first surface external to said housing and extending generally parallel to a longitudinal centerline extending from said proximal end to said distal end and a first groove in said first surface for retaining a fluid-transporting tube; and
a second surface external to said housing and extending generally parallel to said longitudinal centerline and a second groove on said second surface for retaining an optical conduit;

said housing comprising a surface area partially enclosing said second groove and an opening in said surface area;

said electrical connecting device comprising an actuating member disposed below said surface area and operable to selectively establish electrical connections in said electrical connecting device, said actuating member accessible through said opening and comprising a rigid structure extending downwardly below said surface area and intersecting said second groove, said structure having an opening in said structure in alignment with said second groove to allow passage of said optical conduit through said structure, said opening in said structure elongated in the vertical direction to allow movement of said actuating device in the vertical direction in the presence of said optical conduit.

* * * * *